United States Patent [19]

Lombardi, Jr. et al.

[11] 4,362,150

[45] Dec. 7, 1982

[54] PERCUTANEOUS INTRA-AORTIC BALLOON APPARATUS

[75] Inventors: Edward J. Lombardi, Jr., Malden; Harold L. Neuman, Reading; Alfred E. Magro, Woburn; Michael L. Rishton, Reading, all of Mass.

[73] Assignee: Kontron Cardiovascular Inc., Everett, Mass.

[21] Appl. No.: 185,762

[22] Filed: Sep. 10, 1980

[51] Int. Cl.$^3$ ...................... A61B 19/00; A61M 25/00
[52] U.S. Cl. .................................. 128/1 D; 128/344; 604/99
[58] Field of Search ........... 128/1 D, 344, 348, 349 B, 128/DIG. 9

[56] References Cited

U.S. PATENT DOCUMENTS

| | | | |
|---|---|---|---|
| 3,939,820 | 2/1976 | Grayzel | 128/1 D |
| 4,105,022 | 8/1978 | Antoshkiw et al. | 128/349 B |
| 4,243,040 | 1/1981 | Beecher | 128/328 |
| 4,254,773 | 3/1981 | Waldbillig | 128/348 |
| 4,261,339 | 4/1981 | Hanson et al. | 128/1 D |
| 4,276,874 | 7/1981 | Wolvek et al. | 128/1 D |
| 4,287,892 | 9/1981 | Schiff | 128/349 B |
| 4,292,974 | 10/1981 | Fogarty et al. | 128/344 |

*Primary Examiner*—Dalton L. Truluck
*Attorney, Agent, or Firm*—Jon S. Saxe; Bernard S. Leon; George W. Johnston

[57] ABSTRACT

Intra-aortic balloon apparatus is disclosed including a single chamber balloon sealably attached to the end of a catheter for non-surgical insertion into the aorta through the skin as by the standard Seldinger technique. In the preferred embodiment, the extreme end of the balloon is fixedly attached to one end of a separate substantially circumferentially rigid but longitudinally flexible tube open at both ends and disposed within and extending the length of the catheter. The opposite end of the tube remote from the balloon is fixedly attached to means for effecting rotation of the tube within the catheter and thereby result in controlled sequential wrapping and unwrapping of the balloon about the tube. In use, the balloon is pumped in conventional manner via the catheter and access through the tube is provided to the interior of the aorta at the extreme end of the balloon. When the end portion of the tube within the balloon is formed of a relatively flacid or flexible material, it is advantageous to use a stylet or wire member for insertion in and along the length of the tube to prevent bending of the flexible portion when the balloon is wrapped around the tube. The tube also permits use of a guide wire to facilitate passing the balloon through the aorta to its desired location.

32 Claims, 5 Drawing Figures

FIG. 2

PERCUTANEOUS INTRA-AORTIC BALLOON APPARATUS

BACKGROUND OF THE INVENTION

This invention relates to intra-aortic balloon pump apparatus and more particularly to improved percutaneous intra-aortic balloon pumping apparatus.

Conventional intra-aortic balloon pumps are shown and described, for example, in U.S. Pat. Nos. 3,692,018, 3,504,662 and 3,939,820.

With increasing experience, the original indications for intra-aortic balloon pumping in cardiogenic shock due to acute infraction, post-operative severe low cardiac output state, or inability to wean from cardiopulmonary bypass have been extended to include refractory unstable angina in the period before and after infarction, recurrent life-threatening tachyarrhythmias, and preoperative support in the presence of severe left ventricular dysfunction. Recently, intra-aortic balloon pumping has been used both experimentally and clinically to reduce infarct size.

During the first few years following the introduction of the intra-aortic balloon pump for clinical use in 1968, balloon catheters were the subject of considerable development of design efforts. In the 1970's, most of the efforts in the field of intra-aortic balloon pumping were directed mainly toward clarifying the indications for and to reporting large clinical experiences with this therapeutic modality. During this period, no major advances in balloon technology were made. However, attention is again being focused on improving the design of balloon pump catheters. A major disadvantage of the design features of conventional intra-aortic balloon pumps is that they must be inserted by a surgical cutdown of the common femoral artery. Obviously, this results in considerable delay in the application of intra-aortic balloon pumping in situations in which it is indicated.

The only presently known available percutaneous intra-aortic balloon catheter comprises a single chamber balloon sealably disposed at the end of a catheter. The extreme end of the balloon is internally bonded to a stiff wire disposed within the balloon and which terminates at a swivel located at the junction of the catheter and the balloon. The balloon is wrapped around the wire by grasping the catheter and twisting the remote end of the balloon until the desired degree of wrapping is obtained. After the balloon is wrapped, the application of a vacuum to the interior of the balloon is relied on to maintain the balloon in its wrapped condition. Rotation during insertion is advised to tighten any loosening of the balloon wrapping. Neither during nor after insertion is access to the interior of the aorta available and no positive means are provided or possible to insure that the balloon remains fully wrapped during insertion or for effecting unwrapping of the balloon after insertion to insure that the balloon is fully unwrapped before pumping commences. Application of pressure to the interior of the balloon, together with manual rotation of the catheter, is relied on to effect unwrapping of the balloon and permit pumping to begin, and rewrapping of the balloon for removal is neither possible nor recommended. Failures with this type of balloon pump have been encountered in unwrapping of the balloon and in passage of the catheter through the aorta.

SUMMARY OF THE INVENTION

The preferred embodiment of the present invention comprises an intra-aortic balloon pump including a single chamber balloon sealably attached to the end of a catheter for nonsurgical insertion into the femoral common artery through the skin as by the standard Seldinger technique. The extreme end of the balloon is preferably fixedly attached to one end of a spearate and preferably substantially circumferentially rigid but longitudinally flexible tubular member capable of withstanding rotation torque without significant distortion. The tubular member is open at both ends and disposed within and extends the length of the catheter. The catheter is terminated in a bifurcation or wye member, one arm of which receives the tubular member and the other arm of which is adapted for connection to a conventional pumping console for effecting pumping of the balloon through the catheter. The opposite end of the tubular member remote from the balloon is fixedly attached to wrapping means carried by the bifurcation or wye member for effecting rotation of the tubular member within the catheter and thereby result in controlled sequential wrapping and unwrapping of the balloon about the tubular member. In use, the balloon is pumped in conventional manner via the catheter and access to the extreme end of the balloon is provided to the interior of the aorta through the tubular member. When the end portion of the tubular member at the balloon is formed of a relatively soft and flexible material, a stylet or stiff wire member is provided for insertion in and along the entire length of the tubular member to prevent bending of the flexible portion when the balloon is wrapped around the tubular member. The tubular member also permits use of a guide wire to facilitate passing the balloon through the aorta to its desired location.

The present invention permits quick and easy insertion of an intra-aortic balloon pump through the skin using any suitable catherization technique such as the Seldinger technique. The present invention also permits controlled and positive wrapping of the balloon before and during insertion, controlled and positive unwrapping of the balloon after it has been inserted and positive and controlled rewrapping of the balloon prior to removal. The provision of a rotatable tubular member within the catheter and open at both ends in combination with wrapping means carried by the catheter not only provides the positive and controlled wrapping and unwrapping features, but permits both the use of a guide wire to facilitate insertion and access to the interior of the aorta after the balloon has been inserted.

A second embodiment of the present invention which does not provide access to the interior of the aorta comprises the provision of a flexible wire rotatably carried within the catheter, one end being interiorly bonded to the extreme end of the balloon and the other end being fixedly attached to wrapping means carried by a bifurcation or wye member for effecting controlled rotation of the wire within the catheter and thereby result in controlled sequential wrapping and unwrapping of the balloon about the wire. The use of a wire results in the provision of a minimum outside diameter for a wrapped balloon and a minimum inside diameter of the catheter.

There is preferably provided a relatively soft and flexible end portion of the tube or wire having such a degree of flexibility as to provide protection against possible rupture or injury of the aorta by the balloon as it is being inserted into or along the aorta. With the provision of a flexible end portion, during insertion this flexible portion will bend or be deflected and thereby greatly reduce the possibility of injury to or punch a hole in the aorta as might happen if wire, hypodermic tubing or the like is used for the entire length of the inner member.

Where the end portion of the tube is comprised of relatively soft and flexible tubing, it is advantageous to use a stylet or wire removably insertable in the tube and extending its entire length to prevent bending of the flexible portion during winding of the balloon prior to insertion or removal. After the balloon is wound, the stylet is no longer necessary and may be removed.

It is an object of the present invention to provide a new and improved catheter.

It is another object of the present invention to provide a catheter which may be inserted percutaneously.

It is another object of the present invention to provide a balloon catheter that permits controlled sequential wrapping and unwrapping of the balloon.

It is another object of the present invention to provide a balloon catheter that may be inserted percutaneously and that permits both the use of a guide wire and access to the interior of the blood vessel in which it is inserted.

The novel features that are considered characteristic of the invention are set forth in the appended claims; the invention itself, however, both as to its organization and method of operation, together with additional objects and advantages thereof, will best be understood from the following description of a specific embodiment when read in conjunction with the accompanying drawings, in which:

FIG. 5 is a side elevation in cross section of another embodiment of the present invention.

Figure 1:
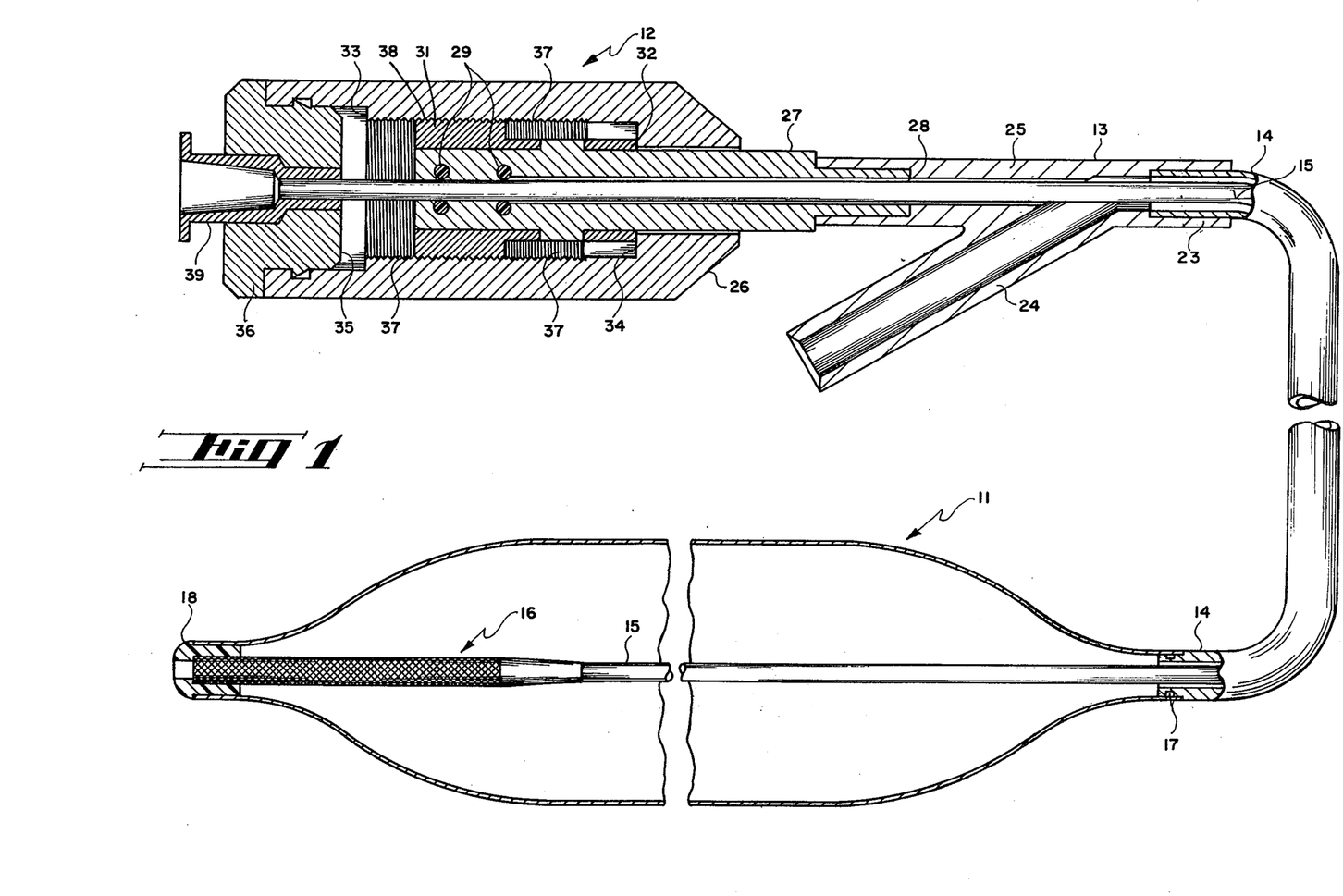
FIG. 1 is a side elevation in cross section of intra-aortic balloon apparatus in accordance with the invention with a portion of the catheter and tube omitted and showing the balloon in the unwrapped condition.

As shown in FIG. 1, a balloon catheter according to the invention includes a conventional single-chamber intra-aortic balloon 11 and rotating means 12 interconnected by a wye 13 and a catheter 14 having rotatably disposed within it a tube or inner lumen 15 as more fully described hereinafter whereby the balloon may controllably be caused to be wrapped and unwrapped. The balloon is illustrated by way of example as a conventional single-chamber intra-aortic balloon.

Figure 2:
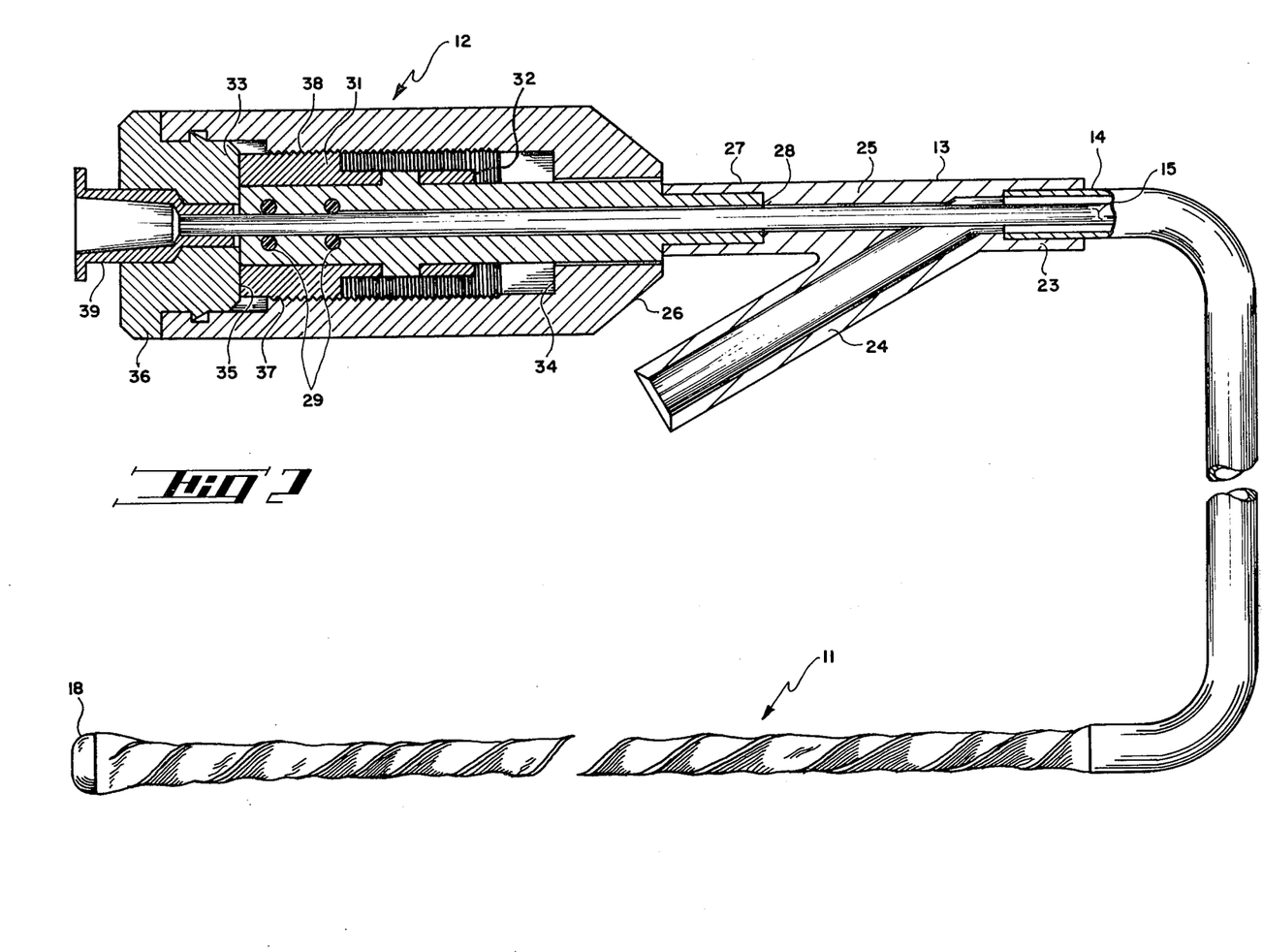
FIG. 2 is a side elevation partially in cross section of the intra-aortic ballon apparatus shown in FIG. 1 showing the balloon in the wrapped condition.

The balloon 11 is preferably formed of an antithrombogenic flexible material and at its proximate end is bonded in fluid-tight manner to the distal end of catheter 14 and is bonded at its distal end to the flexible end portion 16 of the tube 15. As will now be apparent, if the tube 15 is caused to be rotated with respect to catheter 14, the balloon 11 will be caused to be wrapped as shown in FIG. 2 about that portion of the tube 15 disposed within the balloon. The outside diameter of catheter 14 at the point at which it is joined to the balloon 11 is preferably reduced to provide a constant outside diameter. Additionally, a metal ring 17 may be provided at this point to make the proximate end of the balloon more easily visible to facilitate location of the balloon.

Figure 3:
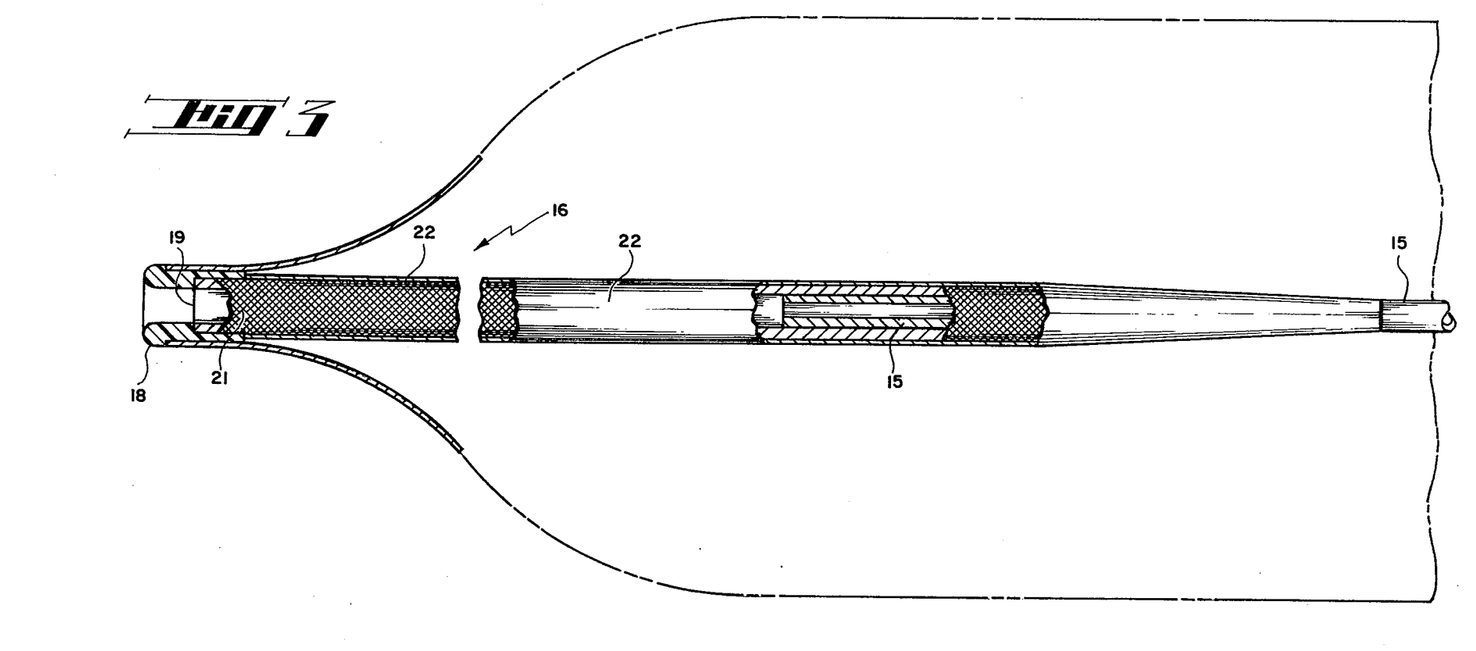
FIG. 3 is a side elevation in cross section on an enlarged scale of a balloon and rotatable tube in accordance with the invention having a soft and flexible end portion.

Directing attention now to the distal end of the balloon as shown in FIGS. 1 and 3, it will be noted that an end portion 16 having preferably a relatively high degree of flexibility is disposed between the tube 15 and a rigid tip 18 sealably bonded to the distal end of the balloon. The rear portion of tip 18 has a reduced outer diameter to receive the tip of the balloon and an enlarged inner diameter to receive the extreme end of the flexible end portion 16. The opposite end of end portion 16 is bonded to the extreme end of tube 15. End portion 16 is of a construction and/or material that, while substantially flexible if not flacid, resists rotational forces to prevent twisting when the balloon is being wrapped. This may be provided, for example, as best shown in FIG. 3 by providing an inner plastic tube 19 covered with wire braid 21 which, in turn, is covered with a heat shrinkable sleeve 32. When the sleeve 22 is shrunk onto the braid 21, this provides a flexible member capable of satisfactorily withstanding reasonable rotational torque resulting from the wrapping of the balloon. The inner tube 19 and braid 21 are disposed within and bonded to the tip 18. The opposite end of the inner tube 19 is fitted over the end of tube 15, an extending portion of the braid 21 is bonded to the tube and covered by the heat shrinkable sleeve 22.

While a particular form of a flexible end portion has been shown and described, other embodiments will readily occur to those skilled in the art and are intended to be included within the scope of the invention. It is only necessary that the flexible end portion, whether solid or hollow, have relatively low resistance to lateral bending, but a high resistance to rotational torque sufficient to withstand rotational torque applied to it by the rotating means without substantial distortion of twisting.

Hypodermic tubing having an inside diameter of 0.038 inch and an outside diameter of 0.050 inch has been found satisfactory for tube 15 and when disposed within a 12 French catheter, permits percutaneous insertion with conventional catheterization apparatus and free flow of gas to and from the balloon during use.

The proximate end of catheter 14 is sealably bonded to a first leg 13 of wye 13 formed of a suitable plastic material such as, for example, a urethane copolymer. A second leg 24 in communication with the first leg 23 is adapted for connection to the console containing conventional pumping means for inflating and deflating the balloon through legs 23 and 24 and catheter 14. The tube 15 freely and rotatably passes coaxially through legs 23 and 25 of wye 13 and extends to and is fixedly attached to the wrapping handle 26 defining the outer portion of the rotating means 12. A wrapping stop and thread member 27 disposed within wrapping handle 26 is fixedly bonded to leg 25 of wye 13 and is provided with a central passage 28 for freely receiving tube 15. Disposed within passage 28 are O-rings 29 to prevent leakage when the balloon is being inflated and deflated. Since, for the embodiment shown in FIG. 1, tube 15 rotates within stop and thread member 27 and all connections in communication with the interior of catheter 14 are of the fluid-tight type, O-rings 29 function to provide a seal at the only possible point of leakage into or out of catheter 14. Fixedly provided on the exterior of the rear portion of stop and thread member 27 as by injection molding is an externally threaded thread member 31 having an unwrapped stop surface 32 and a wrapped stop surface 33. Whereas the stop and thread member 27 may be formed of a urethane copolymer or the like, the external thread member 31 is preferably formed of a harder material such as, for example, an acetal resin in which threads may be cut or molded. The stop surface 32 cooperates with an internal stop surface 34 on the wrapping handle 26 to limit travel of the wrapping handle 26 when rotated to the fully unwrapped position as shown in FIG. 1. Similarly, stop surface 33 cooperates with an internal stop surface 35 on the end cap 36 forming part of the wrapping handle 26 to limit travel of the wrapping handle 26 when rotated to the fully wrapped position as shown in FIG. 2. Wrapping handle 26 is shown in the fully unwrapped position in FIG. 1 and in the fully wrapped position in FIG. 2. The wrapping handle 26 is provided with internal threads 37 to mate with the external threads 38 on the thread member 31.

The threads of the rotating means 12 are preferably of a size and pitch such as, for example, one-half inch in diameter with seventy-two threads per inch, to provide a sufficient number of rotations of the balloon to firmly wrap it on tube 15 without excessively stressing it while providing the minimum amount of longitudinal travel of the wrapping handle 26. Eighteen turns with a travel of about 0.252 inch has been found satisfactory for an intra-aortic balloon having a displacement of 40 CC.

The proximate end of wrapping handle 26 is closed by end cap 36 which may be snapped into the open end of the wrapping handle 26 and bonded thereto after the wrapping handle has been threaded into position. The spacing of stop surfaces 32, 33 and 34, 35 are selected to provide the desired number of rotations of the wrapping handle for the balloon with which it is to be used.

In the event a greater or lesser number of turns or a greater or lesser distance of travel than that discussed herein is desired, this may be simply and easily achieved by the selection of the necessary thread pitch and distance between the stops 32, 34 and 33, 35 to provide the desired number of turns and travel of the wrapping handle.

Axially provided in end cap 36 is a conventional luer fitting 39 to which tube 15 is fixedly attached. Luer fitting 39 is fixedly attached or bonded to end cap 36 whereby when the wrapping handle 26 is rotated, tube 15, being fixedly attached thereto, will also be rotated and thereby effect controlled sequential wrapping and unwrapping of the balloon.

Directing attention now to FIG. 2 which shows the embodiment of FIG. 1 in the fully wrapped position, it will be noted that the diameter of the balloon in its wrapped position is not greater, and in fact is slightly less, than that of catheter 14. This feature facilitates the insertion and removal of the balloon through the sheath member (not shown) typically used in the Seldinger technique of catheterization.

It will also be noted that whereas in FIG. 1, stops 32 and 34 are in abutting relationship, in FIG. 2, stops 32 and 34 are spaced one from another and stops 33 and 35 are in abutting relationship and illustrate the fully wrapped position.

Tube 15 and flexible portion 16 are selected to be of such a length that the balloon may assume its normal fully inflated condition without being stressed or stretched. The provision of rotating means substantially as described above permits only the correct amount of wrapping and unwrapping in every case with insignificant elongation of the balloon during the wrapping operation.

While a particular arrangement and configuration of parts have been shown for the rotating means 12, it is to be understood that other alternate arrangements operating in substantially the same way to provide substantially the same results will occur to those skilled in the art and are included within the scope of the invention. Thus, it is not necessary that rotation of rotating means 12 cause tube 15 to be moved axially while it is effecting wrapping or unwrapping of the balloon, nor is it necessary that sealing means such as O-rings 29 be used or located as shown to prevent leakage of fluid from the catheter. Such alternate embodiments will be obvious to those skilled in the art and are included within the scope of the invention.

It will also be understood that wye 13 may effectively be incorporated in the catheter, or in the rotating means 12, or omitted. In the event wye 13 is omitted, only a fluid flow port means equivalent to arm 24 and in communication with the interior of catheter 14 is necessary.

Figure 4:
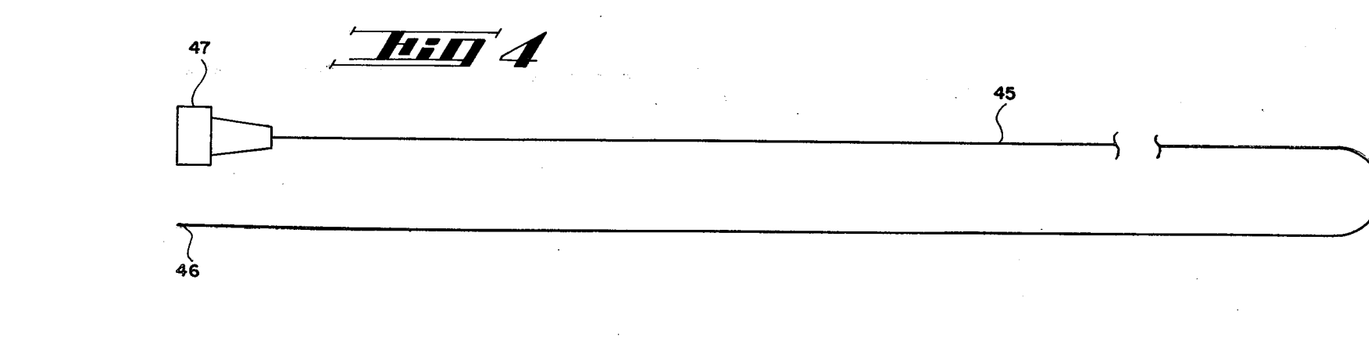
FIG. 4 is a side elevation of a stylet for use with embodiments incorporating a hollow inner lumen having a flexible end portion.
Figure 7:
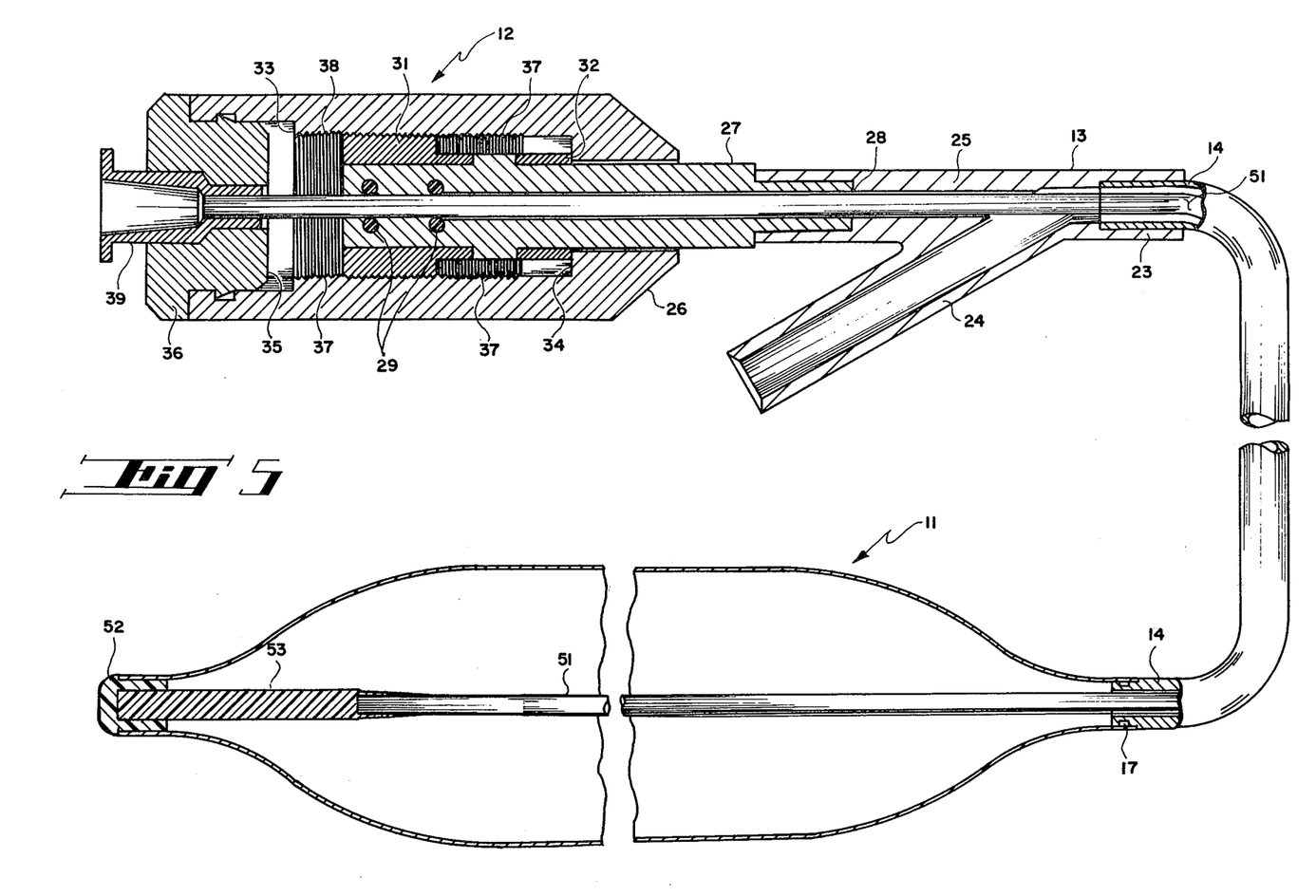

FIG. 4 shows a stylet or wire 45 for insertion into tube 15 prior to effecting wrapping of the balloon when tube 15 is terminated in a flexible portion comprising a portion or all of the length of the balloon. It has been found that in this case, when one attempts to wrap the balloon without the presence of stylet 45, the flexible portion tends to be pulled out of line and adversely affects the wrapping of the balloon. Use of stylet 45 insures that the balloon will be wrapped uniformly.

Stylet 45 is of a length that its distal end 46 is preferably located within tip 18. The proximate end of stylet 45 is terminated in a luer fitting 47 adapted for mating relationship with luer fitting 39 in end cap 36. After the balloon is wrapped, stylet 45 is no longer needed and may be removed.

Directing attention now to FIG. 5, there is shown another embodiment of the invention. The embodiment as shown in FIG. 5 is identical to that shown in FIG. 1 with the exception that a wire member 51 is substituted for tubular member 15.

Wire 51 is fixedly attached at one end to luer 39 and extends through appropriate sized O-rings 29, stop and thread member 27, wye 13, catheter 14 and balloon 11. The distal end of wire 51 is fixedly attached to a flexible end portion 53, the distal end of which is fixedly attached to tip 52 whereby the balloon may be sequentially wrapped and unwrapped in the same manner as described in connection with the embodiment of FIG. 1.

As with hypodermic tubing and the like, wire 51 is comparatively stiff. If such tubing or wire extends to the tip of the balloon, this makes it difficult for the catheter to follow, for example, a partially obstructed or curved blood vessel. While less desirable, it is to be understood that the flexible end portions shown in FIGS. 1, 2, 3 and 5 may, of course, be omitted with a consequent increase in the possibility of injury and/or difficulty in inserting the catheter.

While the embodiment of FIG. 5 permits controlled sequential wrapping and unwrapping of the balloon, it does not permit the use of a guide wire for insertion of the balloon or access to the interior of the blood vessel in which it is inserted. However, the provision of wire 51 does permit controlled wrapping and unwrapping of the balloon as well as a reduction in the diameter of the various components through which it passes as compared to that necessary for the presence of tube 15. The diameter of the balloon in the wrapped position is also reduced.

The various features and advantages of the invention are thought to be clear from the foregoing description. Various other features and advantages not specifically enumerated will undoubtedly occur to those versed in the art, as likewise will many variations and modifications of the preferred embodiment illustrated, all of which may be achieved without departing from the spirit and scope of the invention as defined by the following claims:

We claim:

1. In a balloon catheter appratus including a hollow catheter having a proximate end and a distal end, and an inflatable and deflatable balloon having a proximate end and a distal end, said proximate end of the balloon being sealably attached to the distal end of the catheter for admitting fluid and withdrawing fluid from the balloon, the improved combination comprising:
   (a) a longitudinally flexible metal tubular member having a proximate end portion and a distal end portion and rotatably disposed within and extending the length of the catheter and into the balloon, said distal end portion of the tubular member being fixedly attached to the distal end of said balloon;
   (b) a non-metallic tube portion fixedly attached to said distal end portion of the metal tubular member, said tube portion having relatively low resistance to lateral bending and being circumferentially rigid to withstand rotational torque without substantial distortion; and
   (c) rotating means coupled to the proximate end of said catheter and fixedly attached to the proximate end portion of said tubular member for effecting wrapping and unwrapping of said balloon about said tubular member, said tubular member being rotated with respect to said catheter upon rotation of said rotating means with respect to said catheter, said tubular member defining a continuous open passage from and through said rotating means to and through said balloon.

2. The balloon catheter apparatus of claim 1 wherein the tube portion is covered with a metal braid.

3. The balloon catheter apparatus of claim 2 wherein the metal braid is covered with a heat shrinkable sleeve.

4. The balloon catheter apparatus of claim 1 further comprising rotation limiting means for limiting the rotation of said rotating means to a predetermined number of rotations in either direction of rotation to effect a predetermined degree of wrapping and unwrapping of said balloon.

5. The balloon catheter apparatus of claim 4 wherein the rotation limiting means comprises a first shoulder means having a shoulder positioned within the rotating means and configured for precluding rotation of said rotating means beyond a predetermined number of rotations in a direction of rotation, and a second shoulder means having a shoulder positioned within the rotating means and configured for precluding rotation of said rotating means beyond a predetermined number of rotations in the other direction of rotation.

6. A balloon catheter apparatus comprising:
   (a) a hollow catheter having a proximate end and a distal end;
   (b) an inflatable and deflatable balloon having a proximate end and a distal end, said proximate end of the balloon being sealably attached to the distal end of the catheter;
   (c) an elongated member having a proximate end portion and a distal end portion and rotatably disposed within and extending the length of said catheter into the balloon;
   (d) a tip member having a distal end and a proximate end, said distal end of the tip member being fixedly attached to the distal end of said balloon and the proximate end of the tip member being fixedly attached to the distal end portion of the elongated member at a location disposed from the attachment of the distal end of the tip member to the distal end of the balloon, said tip member having means for low resistance to lateral bending and high resistance to rotational torque when applied through the elongated member; and
   (e) rotating means coupled to the proximate end of the catheter and fixedly attached to the proximate end portion of said elongated member for effecting wrapping and unwrapping of said balloon about said elongated member, said elongated member and tip member being rotated with respect to said catheter upon rotation of said rotating means with respect to said catheter.

7. The balloon catheter apparatus of claim 6 wherein said elongated member is hollow.

8. The balloon catheter apparatus of claim 6 wherein said elongated member and said tip member are hollow and define a continuous open passage from and through said rotating means to and through said balloon.

9. The balloon catheter apparatus of claim 6 wherein said elongated member is solid.

10. The balloon catheter apparatus of claim 6 wherein said elongated member and said tip member are solid.

11. The balloon catheter apparatus of claim 8 wherein said elongated member is a longitudinally flexible metal tubular member and said tip member includes a flexible non-metallic tube portion fixedly bonded to said metal tubular member.

12. The balloon catheter apparatus of claim 11 wherein the tube portion is covered with a metal braid.

13. The balloon catheter apparatus of claim 11 wherein the metal braid is covered with a heat shrinkable sleeve.

14. The balloon catheter apparatus of claim 6 wherein said means for low resistance to lateral bending and high resistance to rotational torque includes:
   (i) a flexible non-metallic member fixedly attached to the distal end portion of the elongated member;
   (ii) a metal braid covering said non-metallic member; and
   (iii) a heat shrinkable sleeve covering said metal braid.

15. The balloon catheter apparatus of claim 6 further comprising fluid flow port means in communication with the interior of said catheter, and wherein said rotating means further includes means for preventing leakage of fluid from said catheter through said rotating means.

16. The balloon catheter apparatus of claim 15 wherein said rotating means further includes rotation limiting means for limiting the rotation of said rotating means to a predetermined number of rotations in either direction of rotation of the rotating means to effect a predetermined degree of wrapping and unwrapping of the balloon.

17. The balloon catheter apparatus of claim 7 wherein said rotating means includes rotation limiting means for limiting the rotation of said rotating means to a predetermined number of rotations in either direction of rotation and second means for preventing leakage of fluid from said catheter through said rotating means.

18. The balloon catheter apparatus of claim 6 further comprising a wye member disposed between said catheter and said rotating means, said wye member having first and second coaxial legs through which said elongated member passes and a third leg providing communication with the interior of said catheter.

19. The balloon catheter apparatus of claim 17 wherein the rotation limiting means comprises a first shoulder means having a shoulder positioned within the rotating means and configured for precluding rotation of said rotating means beyond a predetermined number of rotations in a direction of rotation, and a second shoulder means having a shoulder positioned within the rotating means and configured for precluding rotation of said rotating means beyond a predetermined number of rotations in the other direction of rotation.

20. The balloon catheter apparatus of claim 6 wherein the proximate end of the tip member and the distal end portion of the elongated member are fixedly attached together within the balloon at a location spaced from the location at which the distal end of the tip member is fixedly attached to the distal end of the balloon.

21. A balloon catheter apparatus comprising:
(a) a hollow catheter having a proximate end and a distal end;
(b) an inflatable and deflatable balloon having a proximate end and a distal end, said proximate end of the balloon being sealably attached to the distal end of the catheter;
(c) an elongated member having a proximate end portion and a distal end portion and rotatably disposed within and extending the length of said catheter and balloon, said distal end portion being fixedly attached to the distal end of said balloon;
(d) rotating means coupled to the proximate end of said catheter and fixedly attached to the proximate end portion of said elongated member for effecting wrapping and unwrapping of said balloon about said elongated member, said elongated member being rotated with respect to said catheter upon rotation of said rotating means with respect to said catheter; and
(e) rotation limiting means including first shoulder means having a shoulder positioned within the rotating means and configured for precluding rotation of said rotating means beyond a predetermined degree of rotation in a direction of rotation, and a second shoulder means having a shoulder positioned within the rotating means and configured for precluding rotation of said rotating means beyond a predetermined number of rotations in the other direction of rotation thereby effecting a predetermined degree of wrapping and unwrapping of said balloon.

22. The balloon catheter apparatus of claim 21 wherein the proximate end portion of the elongated member has means for relatively low resistance to lateral bending and high resistance to rotational torque.

23. The balloon catheter apparatus of claim 22 wherein said means for relatively low resistance to lateral bending and high resistance to rotational torque includes:

(i) a non-metallic member fixedly attached to the distal end portion of the elongated member;
(ii) a metal braid covering said non-metallic member; and
(iii) a heat shrinkable sleeve covering said metal braid.

24. The balloon catheter apparatus of claim 22 wherein said elongated member is hollow.

25. The balloon catheter apparatus of claim 24 wherein said elongated member defines a continuous open passage from and through said rotating means to and through said balloon.

26. The balloon catheter apparatus of claim 21 wherein said elongated member is solid.

27. The balloon catheter apparatus of claim 20 further comprising a wye member disposed between said catheter and said rotating means, said wye member having first and second coaxial legs through which said elongated member passes and a third leg providing communication with the interior of said catheter.

28. The balloon catheter apparatus of claim 21 wherein said rotating means further comprises means for preventing leakage of fluid from said catheter through said rotating means.

29. A balloon catheter apparatus comprising:
(a) an inflatable and deflatable balloon having a proximate end and a distal end;
(b) a hollow catheter having a proximate end and a distal end, said distal end being sealably bonded to the proximate end of said balloon for admitting and withdrawing fluid from said balloon;
(c) an elongated member having a proximate end and a distal end and rotatably disposed within and extending the length of said catheter and balloon;
(d) a tip member defining the tip of said balloon distal end, the distal end of said elongated member being fixedly attached to said tip member;
(e) rotating means coupled to the proximate end of said catheter and fixedly attached to the proximate end of said elongated member for effecting wrapping and unwrapping of said balloon about said elongated member, said elongated member being rotated with respect to said catheter upon rotation of said rotating means with respect to said catheter;
(f) rotation limiting means having first shoulder means with a shoulder positioned within the rotating means and configured for precluding rotation of said rotating means beyond a predetermined number of rotations in a direction of rotation, and a second shoulder means with a shoulder positioned within the rotating means and configured for precluding rotation of said rotating means beyond a predetermined number of rotations in the other direction of rotation thereby effecting a predetermined degree of wrapping and unwrapping of said balloon;
(g) fluid flow port means in communication with the interior of said catheter; and
(h) sealing means for preventing leakage of fluid from said catheter through said rotating means.

30. A balloon catheter as recited in claim 29 wherein the end portion including said distal end of said elongated member has a relatively low resistance to lateral bending.

31. A balloon catheter comprising:
(a) an inflatable and deflatable balloon having a proximate end and a distal end;

(b) a hollow catheter having a proximate end and a distal end, said distal end being sealably bonded to the proximate end of said balloon for admitting and withdrawing fluid from said balloon;

(c) an elongated metallic tubular member having an open proximate end and an open distal end and rotatably disposed within and extending the length of said catheter and balloon;

(d) a hollow tip member defining the tip of said balloon distal end, the open distal end of said elongated tubular member being fixedly and coaxially attached to said tip member;

(e) rotating means sealably coupled to the proximate end of said catheter and fixedly attached to the proximate end of said elongated tubular member for effecting wrapping and unwrapping of said balloon about said elongated member, said elongated member being rotated with respect to said catheter upon rotation of said rotating means with respect to said catheter, said open proximate end of said elongated tubular member extending through said rotating means whereby said elongated tubular means defines a continuous open passage from and through said rotating means to and through said balloon;

(f) rotational limiting means for limiting the rotation of said rotating means to a predetermined number of rotations to effect a desired degree of wrapping of said balloon;

(b) fluid flow port means in communication with the interior of said catheter; and (h) sealing means for preventing leakage of fluid from said catheter through said rotating means.

32. A balloon catheter as recited in claim 31 wherein the end portion including said distal end of said tubular member is hollow and formed of flexible non-metallic material having a relatively low resistance to lateral bending.

* * * * *